United States Patent [19]
Johnson

[11] Patent Number: 5,811,641
[45] Date of Patent: Sep. 22, 1998

[54] INBRED CORN LINE LH179

[75] Inventor: Arthur L. Johnson, Williamsburg, Iowa

[73] Assignee: Holden's Foundation Seeds Inc., Williamsburg, Iowa

[21] Appl. No.: 725,920

[22] Filed: Oct. 4, 1996

[51] Int. Cl.$^6$ .............................. A01H 5/00; A01H 4/00; A01H 1/00; C12N 5/04
[52] U.S. Cl. .................. 800/200; 800/250; 800/DIG. 56; 435/412; 435/424; 435/430; 435/430.1; 47/58; 47/DIG. 1
[58] Field of Search ...................................... 800/200, 205, 800/DIG. 56; 47/58, DIG. 1; 435/172.3, 172.1, 411, 412, 424, 430

*Primary Examiner*—Gary Benzion
*Attorney, Agent, or Firm*—Rothwell, Figg, Ernst & Kurz

[57] ABSTRACT

An inbred corn line, designated LH179, is disclosed. The invention relates to the seeds of inbred corn line LH179, to the plants of inbred corn line LH179 and to methods for producing a corn plant produced by crossing the inbred line LH179 with itself or another corn line. The invention further relates to hybrid corn seeds and plants produced by crossing the inbred line LH179 with another corn line.

10 Claims, No Drawings

INBRED CORN LINE LH179

BACKGROUND OF THE INVENTION

The present invention relates to a new and distinctive corn inbred line, designated LH179. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, better stalks and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior corn inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same corn traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new corn inbred line.

The development of commercial corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny. A double-cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop stable, high yielding corn hybrids that are agronomically sound. The reasons for this goal are obviously to maximize the amount of grain produced on the land used and to supply food for both animals and humans. To accomplish this goal, the corn breeder must select and develop corn plants that have the traits that result in superior parental lines for producing hybrids.

SUMMARY OF THE INVENTION

According to the invention, there is provided a novel inbred corn line, designated LH179. This invention thus relates to the seeds of inbred corn line LH179, to the plants of inbred corn line LH179 and to methods for producing a corn plant produced by crossing the inbred line LH179 with itself or another corn line. This invention further relates to hybrid corn seeds and plants produced by crossing the inbred line LH179 with another corn line.

DEFINITIONS

In the description and tables which follow, a number of terms are used. In order to provide a clear and consistent understanding of the specification and claims, including the scope to be given such terms, the following definitions are provided:

Predicted RM

This trait for a hybrid, predicted relative maturity (RM), is based on the harvest moisture of the grain. The relative maturity rating is based on a known set of checks and utilizes conventional maturity systems such as the Minnesota Relative Maturity Rating System.

MN RM

This represents the Minnesota Relative Maturity Rating (MN RM) for the hybrid and is based on the harvest moisture of the grain relative to a standard set of checks of previously determined MN RM rating. Regression analysis is used to compute this rating.

Yield (Bushels/Acre)

The yield in bushels/acre is the actual yield of the grain at harvest adjusted to 15.5% moisture.

Moisture

The moisture is the actual percentage moisture of the grain at harvest.

GDU Silk

The GDU silk (=heat unit silk) is the number of growing degree units (GDU) or heat units required for an inbred line or hybrid to reach silk emergence from the time of planting. Growing degree units are calculated by the Barger Method, where the heat units for a 24-hour period are:

$$GDU = \frac{(Max. + Min)}{2} - 50.$$

The highest maximum used is 86° F. and the lowest minimum used is 50° F. For each hybrid, it takes a certain number of GDUs to reach various stages of plant development. GDUs are a way of measuring plant maturity.

Stalk Lodging

This is the percentage of plants that stalk lodge, i.e., stalk breakage, as measured by either natural lodging or pushing the stalks determining the percentage of plants that break off below the ear. This is a relative rating of a hybrid to other hybrids for standability.

Root Lodging

The root lodging is the percentage of plants that root lodge; i.e., those that lean from the vertical axis at an approximate 30° angle or greater would be counted as root lodged.

Plant Height

This is a measure of the height of the hybrid from the ground to the tip of the tassel, and is measured in centimeters.

Ear Height

The ear height is a measure from the ground to the ear node attachment, and is measured in centimeters.

Dropped Ears

This is a measure of the number of dropped ears per plot, and represents the percentage of plants that dropped an ear prior to harvest.

DETAILED DESCRIPTION OF THE INVENTION

Inbred corn line LH179 is a yellow dent corn with superior characteristics, and provides an excellent parental line in crosses for producing first generation ($F_1$) hybrid corn.

LH179 is a corn inbred line developed from the single cross EX1343×LH85 by selfing and using the pedigree system of plant breeding. Yield, stalk quality, root quality, disease tolerance, late plant greenness, late plant intactness, ear retention, pollen shedding ability, silking ability and corn borer tolerance were the criteria used to determine the rows from which ears were selected.

Inbred corn line LH179 has the following morphologic and other characteristics (based primarily on data collected at Williamsburg, Iowa).

VARIETY DESCRIPTION INFORMATION

1. TYPE: Dent
2. REGION WHERE DEVELOPED: Northcentral U.S.
3. MATURITY:

|  | Days | Heat Units |
|---|---|---|
| From emergence to 50% of plants in silk: | 73 | 1264 |
| From emergence to 50% of plants in pollen | 73 | 1264 |

$$\text{Heat Units:} = \frac{[\text{Max. Temp. } (\leq 86° \text{ F.}) + \text{Min. Temp. } (\geq 50° \text{ F.})]}{2} - 50$$

4. PLANT:
   Plant Height (to tassel tip): 180.6 cm (SD=8.64)
   Ear Height (to base of top ear): 53.5 cm (8.03)
   Average Length of Top Ear Internode: 13.3 cm (1.53)
   Average number of Tillers: 0 (0)
   Average Number of Ears per Stalk: 1.0 (0.0)
   Anthocyanin of Brace Roots: Absent
5. LEAF:
   Width of Ear Node Leaf 9.7 cm (0.72)
   Length of Ear Node Leaf: 73.2 cm (3.32)
   Number of leaves above top ear: 5 (0.42)
   Leaf Angle from 2nd Leaf above ear at anthesis to Stalk above leaf: 25° (4.79)
   Leaf Color: Dark Green—Munsell Code 5 GY 3/4
   Leaf Sheath Pubescene (Rate on scale from 1=none to 9=like peach fuzz): 5
   Marginal Waves (Rate on scale from 1=none to 9=many): 2
   Longitudinal Creases (Rate on scale from 1=none to 9=many): 2
6. TASSEL:
   Number of Lateral Branches: 7 (1.27)
   Branch Angle from Central Spike: 36 (10.30)
   Tassel Length (from top leaf collar to tassel top): 43.7 cm (4.15)
   Pollen Shed (Rate on scale from 0=male sterile to 9=heavy shed): 7
   Anther Color: Yellow—Munsell Code 2.5Y 8/6
   Glume Color: Medium Green—Munsell Code 5GY 5/6
   Bar Glumes: Absent
7a. EAR: (Unhusked Data)
   Silk Color (3 days after emergency): Light Green—Munsell Code 2.5GY 8/6
   Fresh Husk Color (25 days after 50% silking): Medium Green—Munsell Code 2.5GY 7/6
   Dry Husk Color (65 days after 50% silking): Buff—Munsell Code 7.5YR 7/4
   Position of Ear: Upright
   Husk Tightness (Rate on scale from 1=very loose to 9=very tight): 3
   Husk Extension: Medium (<8 cm)
7b. EAR: (Husked Ear Data)
   Ear Length: 13.3 cm (1.53)
   Ear Diameter at mid-point: 39.0 mm (2.0)
   Ear Weight: 72.2 gm (19.49)
   Number of Kernel Rows: 12 (1.23)
   Kernel Rows: Distinct
   Row Alignment: Straight
   Shank Length: 11.9 cm (2.72)
   Ear Taper: Average
8. KERNEL: (Dried)
   Kernel Length: 11.6 mm (0.94)
   Kernel Width: 9.7 mm (0.67)
   Kernel Thickness: 5.0 mm (0.81)
   Round Kernels (Shape Grade): 78.0% (4.50)
   Aleurone Color Pattern: Homozygous
   Aleurone Color: White
   Hard Endosperm Color: Yellow—Munsell code 2.5Y 6/8
   Endosperm Type: Normal Starch
   Weight per 100 kernels (unsized sample): 25.2 gm (0.54)
9. COB:
   Cob Diameter at Mid-Point: 28.1 mm (2.4)
   Cob Color: Light Red—Munsell code 5R 5/6
10. DISEASE RESISTANCE:
    Rating [1=(most susceptible) through 9=(most resistant)]
    3 Eyespot (*Kabatiella zeae*)
    2 Gray Leaf Spot (*Cercospora zeae-maydis*)
    5 Northern Leaf Blight (*Exserohilum turcicum*) race 2
    3 Southern Leaf Blight (*Bipolaris maydis*)
    9 Northern Leaf Spot Race 3 (*H. Carbonum*)
11. AGRONOMIC TRAITS:
    4 Stay Green (at 65 days after anthesis) (Rate on scale from 1=worst to 9=excellent)
    0% Dropped Ears (at 65 days after anthesis)
    0% Pre-anthesis Brittle Snapping
    0% Pre-anthesis Root Lodging
    0% Post-anthesis Root Lodging (at 65 days after anthesis)

This invention is also directed to methods for producing a corn plant by crossing a first parent corn plant with a second parent corn plant, wherein the first or second corn plant is the inbred corn plant from the line LH179. Further, both first and second parent corn plants may be from the inbred line LH179. Therefore, any methods using the inbred corn line LH179 are part of this invention: selfing, backcrosses, hybrid breeding, and crosses to populations. Any plants produced using inbred corn line LH179 as a parent are within the scope of this invention. Advantageously, the inbred corn line is used in crosses with other corn varieties to produce first generation ($F_1$) corn hybrid seed and plants with superior characteristics.

As used herein, the term "plant" includes plant cells, plant protoplasts, plant cell of tissue culture from which corn plants can be regenerated, plant calli, plant clumps, and plant cells that are intact in plants or parts of plants, such as pollen, flowers, kernels, ears, cobs, leaves, husks, stalks, and the like.

Tissue culture of corn is described in European Patent Application, Publication No. 160,390, incorporated herein by reference. Corn tissue culture procedures are also described in Green and Rhodes, "Plant Regeneration in Tissue Culture of Maize", Maize for Biological Research (Plant Molecular Biology Association, Charlottesville, Va. 1982), at 367–372. Thus, another aspect of this invention is to provide for cells which upon growth and differentiation produce the inbred line LH179.

EX1343 and LH85, the progenitors of LH179, are proprietary field corn inbred lines of Holden's Foundation Seeds, Inc. of Williamsburg, Iowa.

LH179 is most similar to LH85. However, the most distinguishing difference is the tassel. The attitude of the main stem and lateral branches of the LH179 tassel are not erect and are perpendicular to the plant. The attitude of the main stem and lateral branches of the LH85 tassel are erect and upright. The tassel of LH179 is not wrapped in the flag leaf and does not "buggywhip") as the tassel is unencumbered and fully exposed. This trait exhibited by LH179 is also not the result of herbicide or other agricultural chemical damage. This trait has been observed at several locations and this phenotypic trait has been consistently expressed. LH179 is darker green in plant color than LH85. When using the Munsell color charts for Plant Tissues as a reference, LH179 would be classified as 5GY 3/4 and LH82 would be classified as 5GY 4/4.

LH179 is an early season field corn inbred line that flowers slightly earlier than LH163. LH179 is a very good pollinator and may have potential use as a seed parent in the northern corn belt. Hybrids containing LH179 have a medium girthy ear and display excellent late season plant appearance.

Some of the criteria used to select ears in various generations include: yield, stalk quality, root quality, disease tolerance, late plant greenness, late season plant intactness, ear retention, pollen shedding ability, silking ability, and corn borer tolerance. During the development of the line, crosses were made to inbred testers for the purpose of estimating the line's general and specific combining ability, and evaluations were run by the Williamsburg, Iowa Research Station. The inbred was evaluated further as a line and in numerous crosses by the Williamsburg and other research stations across the Corn Belt. The inbred has proven to have a very good combining ability in hybrid combinations.

The inbred has shown uniformity and stability for all traits. It has been self-pollinated and ear-rowed a sufficient number of generations, with careful attention to uniformity of plant type to ensure homozygosity and phenotypic stability. The line has been increased both by hand and sibbed in isolated fields with continued observations for uniformity. No variant traits have been observed or are expected in LH179.

TABLES

In the tables that follow, the traits and characteristics of inbred corn line LH179 are given in hybrid combination. The data collected on inbred corn line LH179 is presented for the key characteristics and traits. The tables present yield test information about LH179. LH179 was tested in several hybrid combinations at numerous locations, with two or three replications per location. Information about these hybrids, as compared to several check hybrids, is presented.

The first pedigree listed in the comparison group is the hybrid containing LH179. Information for the pedigree includes:

1. Mean yield of the hybrid across all locations.
2. A mean for the percentage moisture (% M) for the hybrid across all locations.
3. A mean of the yield divided by the percentage moisture (Y/M) for the hybrid across all locations.
4. A mean of the percentage of plants with stalk lodging (% Stalk) across all locations.
5. A mean of the percentage of plants with root lodging (% Root) across all locations.
6. A mean of the percentage of plants with dropped ears (% Drop).
7. The number of locations indicates the locations where these hybrids were tested together.

The series of hybrids listed under the hybrid containing LH179 are considered check hybrids. The check hybrids are compared to hybrids containing the inbred LH179.

The (+) or (−) sign in front of each number in each of the columns indicates how the mean values across plots of the hybrid containing inbred LH179 compare to the check crosses. A (+) or (−) sign in front of the number indicates that the mean of the hybrid containing inbred LH179 was greater or lesser, respectively, than the mean of the check hybrid. For example, a +4 in yield signifies that the hybrid containing inbred LH179 produced 4 bushels more corn than the check hybrid. If the value of the stalks has a (−) in front of the number 2, for example, then the hybrid containing the inbred LH179 had 2% less stalk lodging than the check hybrid.

TABLE 1

OVERALL COMPARISONS
LH74 × LH179 HYBRID VERSUS CHECK HYBRIDS

| Pedigree | Mean Yield | % M | Y/M | % Stalk | % Root | % Drop |
|---|---|---|---|---|---|---|
| LH179 × LH74 (at 13 Loc's) As Compared To: | 151 | 18.11 | 8.33 | 7 | 1 | 1 |
| LH202 × LH163 | −4 | −2.02 | +.63 | +3 | 0 | 0 |
| LH74 × LH163 | −6 | −1.54 | +.37 | +3 | 0 | 0 |
| LH74 × LH85 | −2 | −0.63 | +.19 | +1 | +1 | 0 |
| LH146 × LH172 | +1 | −0.43 | +.24 | 0 | 0 | 0 |
| Pioneer 3751 | −7 | +.31 | −0.51 | −1 | +1 | 0 |
| A632 × LH163 | +8 | +.60 | +.17 | +2 | −1 | 0 |

TABLE 2

OVERALL COMPARISONS
LH202 × LH179 HYBRID VERSUS CHECK HYBRIDS

| Pedigree | Mean Yield | % M | Y/M | % Stalk | % Root | % Drop |
|---|---|---|---|---|---|---|
| LH179 × LH202 (at 15 Loc's) As Compared To: | 152 | 18.91 | 8.03 | 4 | 0 | 0 |
| Pioneer 3751 | 0 | +.35 | −0.15 | −5 | 0 | 0 |
| LH146 × LH82 | +10 | +.73 | +.21 | −9 | −1 | 0 |
| LH168 × LH146 | +1 | +1.21 | −0.52 | 0 | 0 | −1 |

TABLE 3

OVERALL COMPARISONS
LH179 × LH223 HYBRID VERSUS CHECK HYBRIDS

| Pedigree | Mean Yield | % M | Y/M | % Stalk | % Root | % Drop |
|---|---|---|---|---|---|---|
| LH179 × LH223 (at 9 Loc's) As Compared To: | 137 | 17.90 | 7.68 | 6 | 0 | 0 |
| LH223 × LH85 | +5 | −0.64 | +.54 | −4 | 0 | 0 |
| LH145 × A641) (LH164 | +16 | −0.18 | +.95 | −3 | 0 | 0 |
| LH145 × A641) (LH85 | +8 | −0.04 | +.45 | −2 | 0 | 0 |
| LH223 × LH160 | +10 | −0.04 | +.58 | −1 | −1 | 0 |
| LH85 × LH145 | 0 | +.04 | −0.02 | −4 | 0 | 0 |
| LH145 × A641) (LH162 | +29 | +1.43 | +1.08 | −2 | −1 | 0 |

DEPOSIT INFORMATION

Inbred seeds of LH179 have been placed on deposit with the American Type Culture Collection (ATCC), Rockville, Md. 20852, under Deposit Accession Number 97743 on Sep.

26, 1996. A Plant Variety Protection Certificate is being applied for with the United States Department of Agriculture.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. Inbred corn seed designated LH179 having ATCC accession No. 97743.
2. A corn plant produced by growing the seed of claim 1.
3. Pollen of the plant of claim 2.
4. An ovule of the plant of claim 2.
5. An inbred corn plant capable of expressing all the physiological and morphological characteristics of the corn plant of claim 2.
6. A tissue culture comprising regenerable cells of the plant of claim 2.
7. A corn plant regenerated from said tissue culture of claim 6, wherein said corn plant is capable of expressing all the physiological and morphological characteristics of the corn plant of claim 2.
8. A method to produce a hybrid corn seed comprising the steps of:

a) planting in pollinating proximity seeds of corn inbred line LH179 having ATCC No. 97743 and another inbred line;
   b) cultivating corn plants resulting from said seeds until said plants bear flowers;
   c) emasculating the male flowers of the plants of either inbred line;
   d) allowing cross pollination to occur between said inbred lines; and,
   e) harvesting seeds produced on said emasculated plants of the inbred line.

9. A first generation ($F_1$) hybrid corn plant produced by growing said hybrid corn seed of claim 8.
10. Seed derived from the hybrid corn plant of claim 9.

* * * * *